United States Patent [19]

Ross

[11] 3,965,945
[45] June 29, 1976

[54] FILLING AID FOR MEDICANT SYRINGE

[76] Inventor: John D. Ross, Box 5541 NWJC, Senatobia, Miss. 38668

[22] Filed: Sept. 9, 1974

[21] Appl. No.: 504,100

[52] U.S. Cl. .............................. 141/27; 128/218 C; 141/115; 141/369; 222/309
[51] Int. Cl.² ...................... B65B 3/04; A61M 5/18
[58] Field of Search ................ 128/218 C; 141/1, 2, 141/18, 21, 27, 94, 115, 116, 329, 330, 363, 364, 369–373, 375, 378; 222/309, 511, 518

[56] References Cited
UNITED STATES PATENTS

| | | | |
|---|---|---|---|
| 2,792,157 | 5/1957 | Gilman | 222/309 |
| 3,261,509 | 7/1966 | Shevell | 222/309 |
| 3,610,241 | 10/1971 | Le Marie | 141/375 |

Primary Examiner—Richard E. Aegerter
Assistant Examiner—Frederick R. Schmidt
Attorney, Agent, or Firm—Peter J. Murphy

[57] ABSTRACT

A pre-adjustable device to which a medicant syringe may be attached for the filling of the syringe with medicant, to limit the extent of withdrawal of the syringe plunger during filling and thereby prevent inadvertent injection of an overdose of medicant. The device includes an overfill control, to allow for slight overfill of the syringe and subsequent expelling of the overfill medicant and entrapped air.

5 Claims, 6 Drawing Figures

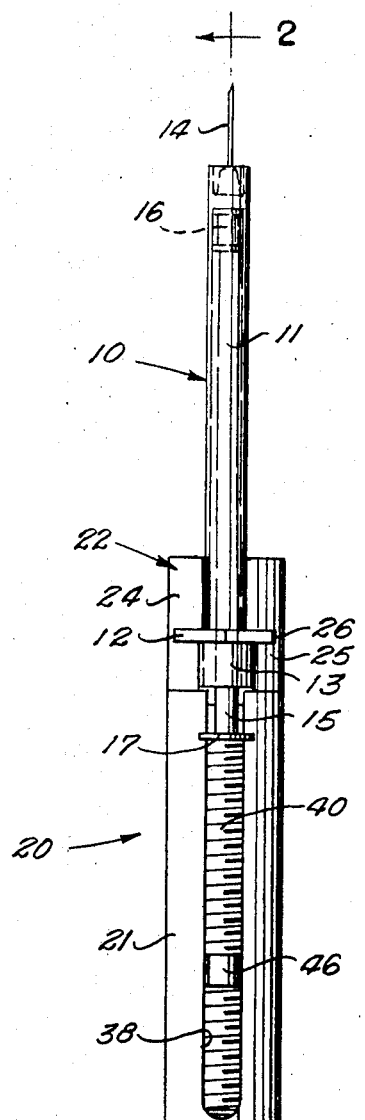
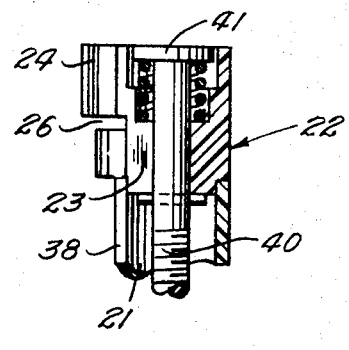
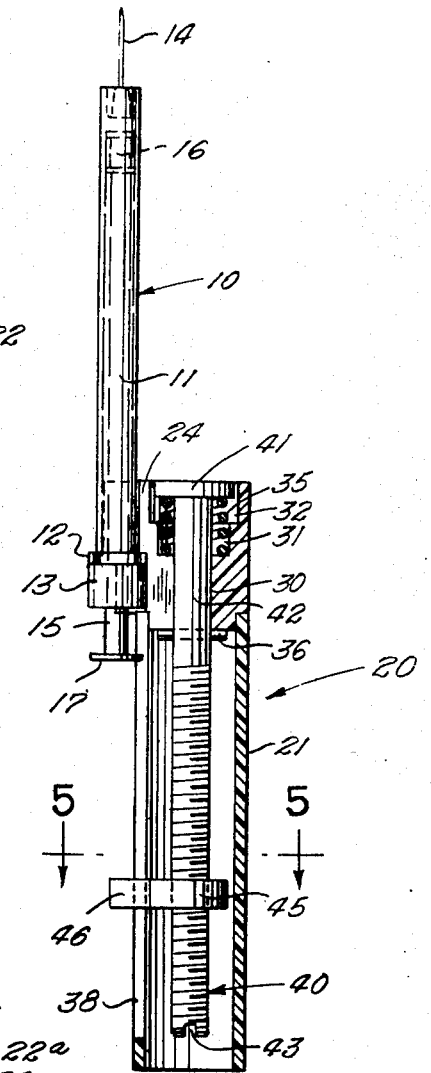
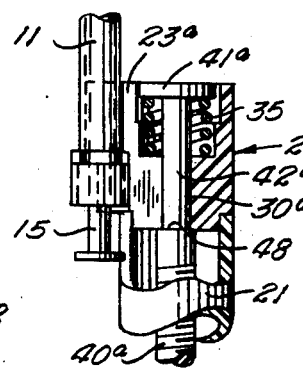
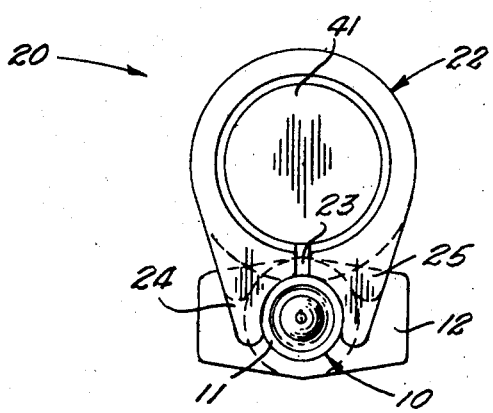
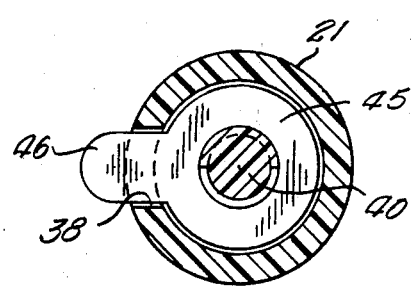

FILLING AID FOR MEDICANT SYRINGE

BACKGROUND AND SUMMARY OF THE INVENTION

This invention relates to a filling aid for a medicant syringe to assist the user in the filling of the syringe and to prevent the loading of the syringe with too much medicant which would result in an overdose injection of the medicant; and more particularly to such device for use by persons who self-administer medicant by means of a syringe, as a safety device to prevent inadvertent excessive filling of the syringe.

This invention is concerned with the problem of assuring accurate dosage of medicant injected by syringe, where the medicant is self-administered or is administered by other members of the household. In many cases the amount of the dosage for each injection is quite critical and, while syringes are marked with gradations to indicate the amount of the dosage, it is relatively easy for users to misread the syringe and therefore inject either an inadequate dose or an excessive dose of medicant. The misreading of the syringe gradations could occur for any number of reasons including obscured indicia on the syringe, poor lighting, simple carelessness, inexperience, or impaired eyesight on the part of the user or the person administering the injection.

A principal object of this invention therefore is to provide a filling aid for medicant syringes, including either disposable or reuseable syringes, which filling aid can be pre-adjusted for use with a particular syringe to limit the amount of medicant which can be received in the syringe and therefore prevent an overdose.

Another object of this invention is to provide such a syringe filling aid which includes an automatic overfill and air ejection control.

A further object of this invention is to provide such a filling aid which can be manufactured at a reasonable cost, which is easy to use, and which is effective and reliable for the intended purpose.

These objects are accomplished in an accessory aid device for use with a medicant syringe which includes an elongated barrel, a needle projecting axially from one end of the barrel, and a plunger projecting from the other end of the barrel. The aid device comprises an elongated body including a hollow sleeve and an end piece secured to one end of the sleeve, the end piece having means for resiliently clamping the syringe barrel thereto, with the longitudinal axis of the syringe and aid device being aligned in parallel relation. The clamping means includes means for preventing relative axial movement of the syringe and aid device. A threaded shaft is disposed within the device being coupled to the end piece for rotation within the body. The body is provided with a longitudinal slot in one wall. A threaded lug is mounted on the shaft for movement therealong in response to rotation of the shaft, the lug having a tab projecting radially into the sleeve slot and disposed to be engaged by the plunger handle of a syringe clamped to the device. The dog is selectively positionable relative to the clamping end piece to limit the extent of withdrawal of the syringe plunger.

The novel features and the advantages of the invention, as well as additional objects thereof, will be understood more fully from the following description when read in connection with the accompanying drawings.

DRAWINGS

FIG. 1 is a side elevation view of a syringe filling aid according to the invention, with a syringe attached thereto in operative relation;

FIG. 2 is a longitudinal sectional view of the syringe filling aid, taken in the plane 2—2 of FIG. 1;

FIG. 3 is an end view of the assembly, as viewed from the top in FIG. 1;

FIG. 4 is a fragmentary sectional view illustrating the clamping end piece of the filling aid; taken in the plane of FIG. 2;

FIG. 5 is a transverse sectional view of the filling aid taken in the plane 5-5 of FIG. 2; and FIG. 6 is a fragmentary view of the assembly of the filling aid and syringe, showing an alternative form of aid construction.

DESCRIPTION OF THE PREFERRED EMBODIMENT

FIGS. 1 through 5 of the drawing illustrate the assembly of a disposable medicant syringe 10 and one preferred form of filling aid device 20. While a disposable type syringe is illustrated and described herein, it is to be understood that the filling aid device may be used as well with any type of syringe including reuseable syringes. The disposable syringe 10, as best seen in FIGS. 1, 2 and 3, is fabricated of a suitable plastic material and includes an elongated transparent barrel 11 having a barrel flange 12 adjacent to one end, and a short barrel extension 13 at that one end. The flange 12 is a radial flange projecting principally from two opposite sides of the barrel to be engaged by two fingers of the user directing injection of the medicant. An axially extending needle 14 is secured at the other end of the barrel. The syringe plunger 15 includes an elongated stem having a piston 16 fixed at its inner end and having a flat cap 17 at its outer end for manipulating the plunger. The barrel is provided with indicia to indicate the amount of medicant in the syringe.

The aid device 20 includes a body which is made up of a cylindrical sleeve 21 and a end piece 22 secured to one end of the sleeve by cementing for example. The end piece is provided with an axial through passage, for accommodating and supporting a threaded shaft 40 to be described, and the end piece is provided with a slot in a radial plane communicating with the passage so that the end piece defines a C-shaped clamping member. The sleeve 21, the end piece 22 and the threaded shaft 40 are all preferably fabricated from a suitable plastic material such as polycarbonate, for example, which is capable of being injection molded; with all parts being tough and resilient; and the end piece particularly should be fabricated of a resilient material to provide for a spring clamping action to be described. Alternatively, the above described body 21, 22 could be fabricated as a one-piece part molded from a suitable plastic material.

Referring now particularly to the configuration of the end piece 22, FIG. 3 is a view of the assembly from the end piece end illustrating the slot 23 and bifurcated clamping jaws 24 and 25. The jaws are divided axially by a transverse groove 26, which is dimensioned to receive the syringe barrel flange 12, and thereby prevent relative axial movement of the syringe. This configuration is particularly illustrated in FIG. 4 which shows the device end piece 22 separate from the syringe 10.

The jaws 24 and 25 define a socket for receiving the syringe barrel 11, which is dimensioned slightly smaller than the barrel so that when the barrel is forced between the jaws in the indicated relation, the syringe will be securely held by the filling device 20 and yet the syringe will be readily removable from the device at the desired time.

Referring now to the threaded stud 40 and the coacting supporting structure of the end piece 22, the stud 40 includes a flat head 41 at one end and an adjacent nonthreaded shank 42. A screwdriver slot 43 is provided at the opposite end of the shaft. This shaft is received in the end piece passage, which is a stepped bore consisting of a small bore portion 30 dimensioned to receive the shaft shank with a sliding fit, an intermediate counterbore 31, and a large counterbore 32 opening to the distal end of the end piece. The large counterbore is dimensioned to receive the head 41 with a sliding fit and defines a shoulder to limit inward movement of the head. The intermediate counterbore 31 defines a recess and shoulder for receiving and confining an overfill compression spring 35 surrounding the shank 42, and confined between this shoulder and the shaft head 41 tending to urge the shaft head out of the end piece 21. Movement of the shaft in this direction is limited however by a transverse stop pin 36 secured in the shaft, by cementing for example. This provides the overfill feature to be described in connection with the operation of the filling aid.

A threaded lug 45 is threaded onto the threaded shaft 40, and includes a radially projecting tab 46 which extends into and through a longitudinal slot 38 provided along one side of the body sleeve 21, this slot permitting longitudinal movement of the lug 45 while preventing relative rotation. As best seen in FIG. 2, the lug tab 46 projects from the slot a sufficient distance to be disposed in the path of movement of the syringe plunger and to be engaged by the plunger cap 17. The shaft head 41 is fully received within the bore 32 at all times and the slotted end of the shaft is protected within the sleeve 21 to obviate inadvertent misadjustment of the lug and minimize tampering with the adjustment.

The slot 38 is generally coextensive with the sleeve 21 and opens to the end of the sleeve secured to the end piece, with the sleeve slot communicating with the end piece slot 23 so as not to interfere with the resilient clamping function of the clamping jaws 24 and 25.

In the assembly of the above described filling aid device 20, the sleeve 21 and end piece 22 would first be secured together, if they are separate parts. The overfill spring 35 would then be placed over the shaft shank and the shaft 40 would be inserted through the end piece passage to be threadedly engaged with the lug 45 which, simultaneously, is placed in position within the sleeve 21. The stop pin 31 would then be secured in any suitable manner within a transverse bore in the shaft 40, the pin being inserted through the sleeve slot 38.

OPERATION

The operation and use of the filling aid illustrated in FIGS. 1 through 5 will now be described briefly. To adjust the filling aid to a particular syringe or a particular model of syringe, the syringe is secured to the aid device in the described manner. The plunger is then withdrawn to position the inner end of the piston at the indicia indicating the desired dosage; and the threaded lug 45 is adjusted axially to the point where it just meets the plunger tab 17, through rotation of the shaft 40 by means of a screwdriver or coin for example. The plunger 40 is normally maintained in the illustrated position by the spring 35, which position is defined by the stop pin 36. In preferred form the shaft head 41 is fully received within the large counterbore 32 and the screw slot end of the shaft is well protected by the sleeve 21 so that there can be no inadvertent turning of the shaft to disturb the preset adjustment.

After the pre-adjusting of the filling aid, the device may be used many times with the same syringe or same model syringe, to administer the selected dosage. For each use of the filling aid, then, the following steps would be observed:

1. The syringe 10 is assembled in clamping relation to the filling aid 20.
2. The plunger is withdrawn to the point of engagement with the lug 45.
3. The syringe needle is inserted into the medicant container.
4. The plunger is pushed fully into the syringe barrel to inject air into the medicant container.
5. The assembly of aid device, syringe and medicant container may be inverted to bring the medicant in contact with the needle, and the plunger withdrawn to the point of engagement with the lug 45 to draw medicant into the syringe.
6. To assure ejection of any entrapped air from the syringe, the plunger is further withdrawn with the lug 45 and shaft 40, with the shaft head 41 compressing the spring 35; and this movement is limited by engagement of the head with the large bore shoulder. This is done with the assembly still inverted, and is a continuation of Step 5.
7. The plunger and lug are then released with the assembly inverted, permitting the spring to move the shaft to the illustrated position limited by the stop pin 36, whereby the overfill fluid and entrapped air are ejected from the plunger back into the medicant container.
8. Remove the syringe needle from the medicant container.
9. Remove the syringe from the filling aid 20.
10. Inject the medicant in the usual manner.

The above mentioned steps 6 and 7 define the overfill procedure which provides for overfilling of the syringe and subsequent ejection of the overfill medicant along with any entrapped air. This feature is essentially automatic, providing the safety feature of ejecting the air and yet maintaining the desired ultimate dose within the syringe.

EMBODIMENT OF FIG. 6

FIG. 6 of the drawing illustrates a slight modification of the structure including a modified end piece 21a and shaft 40a. In this modification the shank portion 42a of the shaft 40a is of reduced diameter relative to the threaded portion, thereby defining a shoulder 48 which engages the inner face of the end piece 21a to define the limiting stop for movement of the shaft 41a in the direction urged by the spring 35.

The device of FIG. 6 functions in the manner identical to the device above described, with the shoulder stop 48 serving the function of the stop pin 36 in the first described embodiment. In the assembly of the device in this form, assuming that the shaft 40a is a unitary member, the threaded portion of the shaft would have to be first inserted through the small bore 30a by spreading the clamping jaws since this small bore is dimensioned for a sliding fit with the reduced diameter shank 42a.

What has been described is a unique, effective and convenient filling aid device for use with medicant syringes to assure the consistent filling of syringes with an absolutely correct dosage of medicant. A particular feature of the aid device is its construction enabling the parts to be fabricated from a suitable plastic material by injection molding methods. An important feature of the filling aid device is the built-in mechanism for the overfilling and subsequent ejection of the overfill medicant and entrapped air, which is necessary to assure that no air remains in the syringe at the time of injection. Another feature of the device is the structure and arrangement enclosing and protecting the threaded adjustment shaft obviate inadvertent misadjustment and tampering with the device.

A particular advantage of the device is its ease of use, enabling use by elderly people and adolescents with utmost safety.

While preferred embodiments of the invention have been illustrated and described, it will be understood by those skilled in the art that changes and modifications may be resorted to without departing from the spirit and scope of the invention.

What is claimed is:

1. An aid device for use with a medicant syringe which includes an elongated barrel, a needle projecting axially from one end of the barrel, and a plunger projecting from the other end of the barrel; said device comprising:

an elongated body including a hollow sleeve and an end piece secured to one end of the sleeve; said body end piece having means for clamping the barrel of a medicant syringe thereto, with the longitudinal axis of the syringe barrel aligned in parallel relation with the longitudinal axis of said body, and including means for preventing axial movement of the syringe barrel relative to said aid device;

an elongated, threaded shaft disposed longitudinally within said body, and mounted in said end piece for relative rotation and limited relative axial movement; said body sleeve having a longitudinal slot in one side wall; a lug threadedly mounted on said threaded shaft having a tab projecting radially through said body slot, whereby rotation of said shaft effects longitudinal movement of said lug along said body;

said lug tab being disposed to be engaged by the plunger of said medicant syringe clamped to said device; and said lug being selectively positionable relative to said body end piece, to limit the extent of withdrawal of the syringe plunger;

said threaded shaft being mounted within said device end piece for limited axial reciprocating movement, said end piece and said shaft having coacting stop means for limiting said reciprocating movement;

spring means for normally urging said shaft to its limiting position toward the end piece end of said device; and said reciprocating shaft movement defining an overfill control, allowing overfill of the syringe and subsequent ejection of the overfill medicant to remove any entrapped air.

2. A device as set forth in claim 1
said shaft being disposed entirely within said body, and provided with means at its threaded end engagable by a suitable actuating tool for rotating said shaft relative to said body.

3. A device as set forth in claim 1
said threaded shaft including an enlarged head at one end; said end piece including a bore dimensioned to receive said shaft in sliding relation and provided with a counterbore dimensioned to receive said shaft head;
said spring means comprising a helical compression spring encircling said shaft and confined in said counterbore by said shaft head;
and said shaft including stop means coacting with the inner face of said end piece to limit movement of said shaft in the direction urged by said spring.

4. A device as set forth in claim 3
said shaft stop means being defined by a transverse pin secured in said shaft and projecting radially therefrom.

5. A device as set forth in claim 3
said shaft including a reduced diameter shank portion between said head and the threaded portion thereof; said shank portion dimensioned for a sliding fit within said end piece bore; and said reduced diameter shank portion defining a shoulder confronting said head and coacting with said end piece to define said stop means limiting movement of said shaft in the direction urged by said spring.

* * * * *